(12) United States Patent
Gebauer

(10) Patent No.: US 9,597,610 B2
(45) Date of Patent: *Mar. 21, 2017

(54) PACKING SYSTEM AND METHOD FOR CHROMATOGRAPHY COLUMNS

(71) Applicant: GE HEALTHCARE BIOPROCESS R&D AB, Uppsala (SE)

(72) Inventor: Klaus Gebauer, Uppsala (SE)

(73) Assignee: GE Healthcare BioProcess R&D AB, Uppsala (SE)

( * ) Notice: Subject to any disclaimer, the term of this patent is extended or adjusted under 35 U.S.C. 154(b) by 267 days.

This patent is subject to a terminal disclaimer.

(21) Appl. No.: 13/672,819

(22) Filed: Nov. 9, 2012

(65) Prior Publication Data

US 2013/0061941 A1 Mar. 14, 2013

Related U.S. Application Data

(63) Continuation-in-part of application No. 12/042,363, filed on Mar. 5, 2008, now Pat. No. 8,778,187.

(30) Foreign Application Priority Data

Mar. 9, 2007 (GB) .................................. 0704603.0

(51) Int. Cl.
| | | |
|---|---|---|
| *B01D 15/20* | (2006.01) | |
| *B01D 15/22* | (2006.01) | |
| *G01N 30/56* | (2006.01) | |
| *B01D 15/14* | (2006.01) | |
| *G01N 30/60* | (2006.01) | |

(52) U.S. Cl.
CPC ............ *B01D 15/206* (2013.01); *G01N 30/56* (2013.01); *B01J 2220/56* (2013.01); *G01N 30/603* (2013.01); *G01N 30/606* (2013.01); *G01N 30/6021* (2013.01); *G01N 2030/565* (2013.01); *Y10T 137/0402* (2015.04)

(58) Field of Classification Search
CPC ........ B01D 15/08; B01D 15/14; B01D 15/22; B01J 2220/56; G01N 30/60; G01N 30/6021; G01N 30/603; G01N 30/606
USPC ............................. 210/656; 73/61.53, 61.56
See application file for complete search history.

(56) References Cited

U.S. PATENT DOCUMENTS 4,350,595 A * 9/1982 Gunkel .................. G01N 30/56
210/198.2
4,549,584 A * 10/1985 Morin .................. B01D 15/206
141/12
(Continued)

FOREIGN PATENT DOCUMENTS

EP 1 698 895 9/2006
GB 2 258 415 2/1993
(Continued)

OTHER PUBLICATIONS

Yip, K., Introduction to Biochemical Engineering, Types of Chromatography, 1997.

*Primary Examiner* — Katherine Zalasky
(74) *Attorney, Agent, or Firm* — WOOD IP LLC

(57) ABSTRACT

The invention relates to a system for packing chromatography columns with a chromatography medium and packing method for use in such columns. In particular, the invention relates to a method and system for packing chromatography columns where the column and chromatography media are pre-sterilized.

8 Claims, 7 Drawing Sheets

(56) References Cited

U.S. PATENT DOCUMENTS

| | | | |
|---|---|---|---|
| 4,597,866 A * | 7/1986 | Couillard | G01N 30/56 210/198.2 |
| 4,737,292 A | 4/1988 | Ritacco et al. | |
| 4,769,141 A * | 9/1988 | Couillard | G01N 30/56 210/198.2 |
| 4,888,112 A * | 12/1989 | Kronwald | G01N 30/6026 210/198.2 |
| 4,927,531 A * | 5/1990 | Sakamoto | B01D 15/206 210/198.2 |
| 5,141,635 A * | 8/1992 | LePlang | B01D 15/08 210/198.2 |
| 5,167,809 A * | 12/1992 | Mann | G01N 30/56 210/189 |
| 5,169,522 A | 12/1992 | Shalon et al. | |
| 5,282,973 A | 2/1994 | Mann | |
| 5,324,426 A * | 6/1994 | Joseph | B01D 15/14 210/198.2 |
| 5,378,365 A * | 1/1995 | Arrighi | C07K 14/745 210/635 |
| 5,423,982 A | 6/1995 | Jungbauer et al. | |
| 5,667,675 A * | 9/1997 | Hatch | B01D 15/206 210/198.2 |
| 5,693,223 A * | 12/1997 | Yamada | B01D 15/08 210/198.2 |
| 5,893,971 A | 4/1999 | Shalon et al. | |
| 5,902,485 A | 5/1999 | Davis et al. | |
| 5,951,873 A | 9/1999 | Shalon et al. | |
| 6,090,279 A * | 7/2000 | Davis | B01D 15/206 210/198.2 |
| 6,171,486 B1 * | 1/2001 | Green | B01D 15/22 210/198.2 |
| 6,190,560 B1 | 2/2001 | Mann | |
| 6,524,484 B2 | 2/2003 | Davis et al. | |
| 6,576,124 B2 * | 6/2003 | Pichl | B01D 15/22 210/198.2 |
| 8,778,187 B2 * | 7/2014 | Gebauer | 210/656 |
| 2003/0098280 A1 | 5/2003 | Davis et al. | |
| 2003/0146159 A1 | 8/2003 | Guiochon | |
| 2003/0183566 A1 | 10/2003 | Laub et al. | |
| 2006/0166816 A1 | 7/2006 | Zhang et al. | |
| 2007/0012626 A1 | 1/2007 | Andersson et al. | |

FOREIGN PATENT DOCUMENTS

| | | |
|---|---|---|
| WO | WO 96/10451 | 4/1996 |
| WO | WO 98/34708 | 8/1998 |
| WO | WO 99/24137 | 5/1999 |
| WO | WO 2005/009585 | 2/2005 |
| WO | WO 2008/009412 | 1/2008 |
| WO | WO 2008/110291 | 9/2008 |

* cited by examiner

PACKING SYSTEM AND METHOD FOR CHROMATOGRAPHY COLUMNS

FIELD OF THE INVENTION

The present invention relates to a system for packing chromatography columns with a chromatography medium and packing method for use in such columns. More specifically, the invention relates to packing systems and methods for improving the packing of chromatography media into chromatography columns.

BACKGROUND OF THE INVENTION

Columns used in liquid chromatography typically comprise a tubular body enclosing a porous chromatography medium through which a carrier liquid flows, with separation taking place by material collection between the carrier liquid and solid phase of the porous medium. Prior to any separation process, the bed has to be prepared starting from the slurry of particles that has to be introduced into the column. The process of bed formation is called 'the packing procedure' and a correctly packed bed is a critical factor influencing the performance of a column containing a packed bed. The goal of the packing procedure is to provide a bed compressed by the optimum amount of compression—the optimum compression factor.

In detail, the porous medium is formed by consolidating a suspension of discrete particles, known as "slurry" that is pumped or poured or sucked into the column, usually from one end. Consolidation of the slurry into a packed bed is typically achieved by filtering it against a particle retaining filter and further compressing the formed filter cake so that it is packed into a volume which is less than the volume that it would have occupied if it had sedimented under the influence of only gravity to form a sedimented bed. The degree of compression depends upon the type of chromatography medium and typically ranges from in between 2-20%. The efficiency of subsequent chromatographic separations relies on the liquid distribution and collection system at the fluid inlet and outlet of the packed bed, but primarily on the homogeneity and stability of the packed bed formed. If the packed bed is not homogeneous and stable a deleterious effect will be experienced for chromatographic separations performed on the bed. Homogeneity and stability of the packed bed depend upon the optimum degree of compression, which must be determined experimentally for each column size (width or diameter), bed height and bed medium.

Several methods are known in the art for packing columns (see, for example, US 2003/0146159). "Flow packing" is a method typically utilised for the preparation of analytical columns (i.e. columns of about 1-10 mm column diameter) and semi-preparative columns (i.e. columns of 10-100 mm column diameter) or even larger. In flow packing, one end of a column is closed by a frit or a filter. At the other end, a slurry or suspension of the packing material is pumped or poured into the column tube. A filtration bed builds up against the frit and grows until a filter cake has formed. The bed is then compressed further to its "target bed height" by percolating a number of column volumes (ca. 3-10) of a packing solvent at a flow rate that is higher than the flow rates used in operation. Consolidation and subsequent compression take place under the influence of the seepage force, that is the reaction of the bed to the pressure gradient required to maintain the flow rate of the stream of liquid percolating through the bed. Once the bed is compressed by the flow, the flow is stopped, the outlet at the bottom of the column is closed and an adapter or upper end cell is adjusted to the target height of the compressed bed. This adjustment is done quickly to avoid a relaxation of the compressed bed exceeding the target bed height.

The flow packing method has the disadvantage that beds of packing material compressed in this manner are axially heterogeneous during the flow compression step yielding highest compression close to the outlet of the column and zero compression at the top of the packed bed. This results in a major relaxation of the bed and a possible re-arrangement of the particles once the packing flow has been stopped and the upper end cell has been brought into position. The gradient in bed compression inherent to this method may result in poor bed stability and poor column efficiency depending on the type of medium and the packed bed geometry.

Standard methods of flow packing may not be suitable for the wide bore columns used in preparative chromatography. Among other factors, it is often undesirable to design equipment that requires application of a packing flow rate and thus a packing pressure substantially higher than the pressure required for subsequent operation. To remedy this problem, packing methods relying on mechanical axial compression are used. Axial compression methods achieve the bed compression by an axial movement of the adapter (end cell). Hereby, the need for high liquid pressure in the column space during packing is removed. A further advantage of the axial compression method is that the bed is compressed homogeneously in axial direction, which avoids the problems of relaxation and particle re-arrangements that occur with the flow packing method.

Radial gradients in bed compression and bed voidage occur with both methods described, which is due to wall friction effects. The impact of the radial heterogeneity depends on the bed geometry, i.e. the ratio of diameter to height. As described above, it is the gradient of compression and bed voidage in axial direction that is substantially different between the flow packing method and the axial compression method.

A disadvantage of axial compression is that columns packed using this method require a means for moving the end cell and a means for controlling this movement. Typical methods for the movement are motor drives or hydraulic systems. As these are attached to or built in to the column, the cost and mechanical complexity of axial compression columns is substantially higher than for flow packing columns.

Prior to any consolidation and compression the medium has to be introduced into the column. Large scale columns are preferably prepared by injecting slurry through a central slurry nozzle or valve into the column. This enables a closed system approach which is preferable for sanitary reasons. Columns based on a slurry valve design may be designed for axial compression packing using a movable adapter or for flow packing using a fixed end cell.

DEFINITIONS

"Analyte" shall be defined as a substance, compound or chemical of natural or synthetic origin, or a reaction product or derivative or metabolite thereof. For the avoidance of doubt, the term shall include biological molecules, such as proteins, peptides, amino acids and nucleic acids, and synthetic molecules such as drugs and/or pro-drugs.

"Medium" shall be defined as any material in which a chromatographic separation is effected. Examples of medium include, but are not limited to, materials which effect ion exchange chromatographic separation, size exclusion chromatographic separation, affinity binding chromatographic separation and reverse phase chromatographic separation.

A "disposable" column is characterized by a pre-treatment of the chromatography medium in order to reduce installation and qualification/validation work otherwise required with non-disposable columns. As a minimum, the pre-treatment involves the formation of the bed of porous medium. Additional pre-treatment can be reduction of microbiological burden, sterilization, depyrogenation etc.

Disposable column may be used as single-use columns, which means that the user is not performing cleaning regimes that require qualification (e.g. testing, validation, etc) of the packed bed before repeated use.

One embodiment of a disposable column is a complete column that is delivered pre-packed with chromatography medium.

Another embodiment of a disposable column consists of a first device representing a frame or vessel designed to resist pressure and load exerted on one or multiple lateral surfaces of the packed bed during operation in order to provide dimensional stability for a packed bed, and a second device, representing a container, shell, cartridge, bag or the like containing the porous medium or bed that is attached to the first device for operation. With the latter embodiment, the porous medium is contained in the secondary container and can be replaced while the frame is re-usable. In this case, the degree of compression of the porous medium required for operation may be adjusted after inserting the contained medium into the frame (see, for example US2002/0166816 and WO2005/009585).

By "non-integral to and external to the column drive means" is meant a drive means which is a separate entity which is only used when packing the column and is removed or detached from the column in its operation. Thus, when the end user operates the column the drive means is not present and attached to the column.

SUMMARY OF THE INVENTION

The object of the invention is to provide a packing method which overcomes the drawbacks of the prior art methods.

The main advantage of the invention is that the packed bed is prepared by the axial compression method yielding advantages of improved bed stability and high column efficiency without the need for high mechanical complexity in the column construction required by conventional solutions for axial compression columns. This allows for a substantial cost reduction.

Yet another advantage of the method of the invention is that it is compatible with low-pressure fluid handling equipment (e.g. a peristaltic pump) as the compression is achieved primarily by the external drive means, such as a compression frame, rather than by the high pressures required by flow compression.

Yet another advantage of the method of the invention is that the packing/filling of the column can be performed as a closed system, which means that the column may even be filled/packed under aseptic conditions starting from a pre-sterilized column and pre-sterilized chromatography medium. The method can therefore be used on "ready-to-process" or "disposable" columns.

Still a further advantage is that the chromatography column is scalable (i.e. increasing or decreasing the column size leads to a predictable performance). This is due to the fact that the filling of the column via the slurry nozzle is done prior to the axial compression step at an elevated adapter position. This allows for homogeneous distribution of the slurry over the cross-sectional area of the column compared to flow packing using a nozzle based on one designed with fixed end cells (for example, see U.S. Pat. No. 6,524,484). For the latter, the packing has to be performed at a constant bed height, the target bed height, which may lead to radial gradients in packed bed density and compression, respectively.

Another advantage of the method of the invention is that the column does not need to be as long as axial compression columns of the prior art because not all of the slurry needs be introduced into the column prior to the commencement of bed formation.

A further advantage of the invention is that a minimum adapter (end unit) stroke is required compared to systems using known methods and thus allows for a more compact construction.

According to a first aspect of the invention, there is provided a method for packing an axial flow chromatography column with a bed of particulate medium of a target bed height,
    said column comprising:
    a housing comprising an elongated tubular side wall;
    opposed, axially spaced first and second end units separated by said side wall,
    wherein at least one said unit is axially movable by drive means relative to the other said unit;
    a first filter adjacent to said first unit and a second filter adjacent to said second unit which together with the side wall define an enclosed bed space for containing a bed of particulate medium and wherein relative movement of the first and/or second filter alters the bed height;
    said first end unit comprising a first valve means for filling of the bed space with said particulate medium; and a first port for adding a liquid to or removing a liquid from the bed space;
    the second end unit comprising a second port for adding a liquid to or removing a liquid from the bed space;
    said method comprising:
    i. adjusting the axial spacing between the first and second filters to a distance greater than that of the target bed height;
    ii. introducing a suspension of the particulate medium into the bed space via the first valve means to provide a bed of particulate medium therein;
    iii. compressing the bed of particulate medium to produce the target bed height by axial movement of the first and/or second end filters;
        wherein said axial flow chromatography column and said suspension of particulate medium are pre-sterilized.

According to a second aspect of the invention, there is provided a system for packing an axial flow chromatography column with a bed of particulate medium of a target bed height, said system comprising:
    i. a column comprising
        a housing comprising an elongated tubular side wall;
        opposed, axially spaced first and second end units separated by said side wall, wherein at least one said unit is axially movable by drive means relative to the other said unit;
        a first filter adjacent to said first end unit and a second filter adjacent to said second end unit which together with the side wall define an enclosed bed space for containing a bed of particulate medium and wherein relative movement of the first and/or second filter alters the bed height;

the first end unit comprising a first valve means for filling of the bed space with said particulate medium; and a first port for adding a liquid to or removing a liquid from the bed space;

the second end unit comprising a second port for adding a liquid to or removing a liquid from the bed space;

ii. a drive means.

wherein said axial flow chromatography column and said suspension of particulate medium are pre-sterilized.

DETAILED DESCRIPTION OF THE INVENTION

Figure 1:
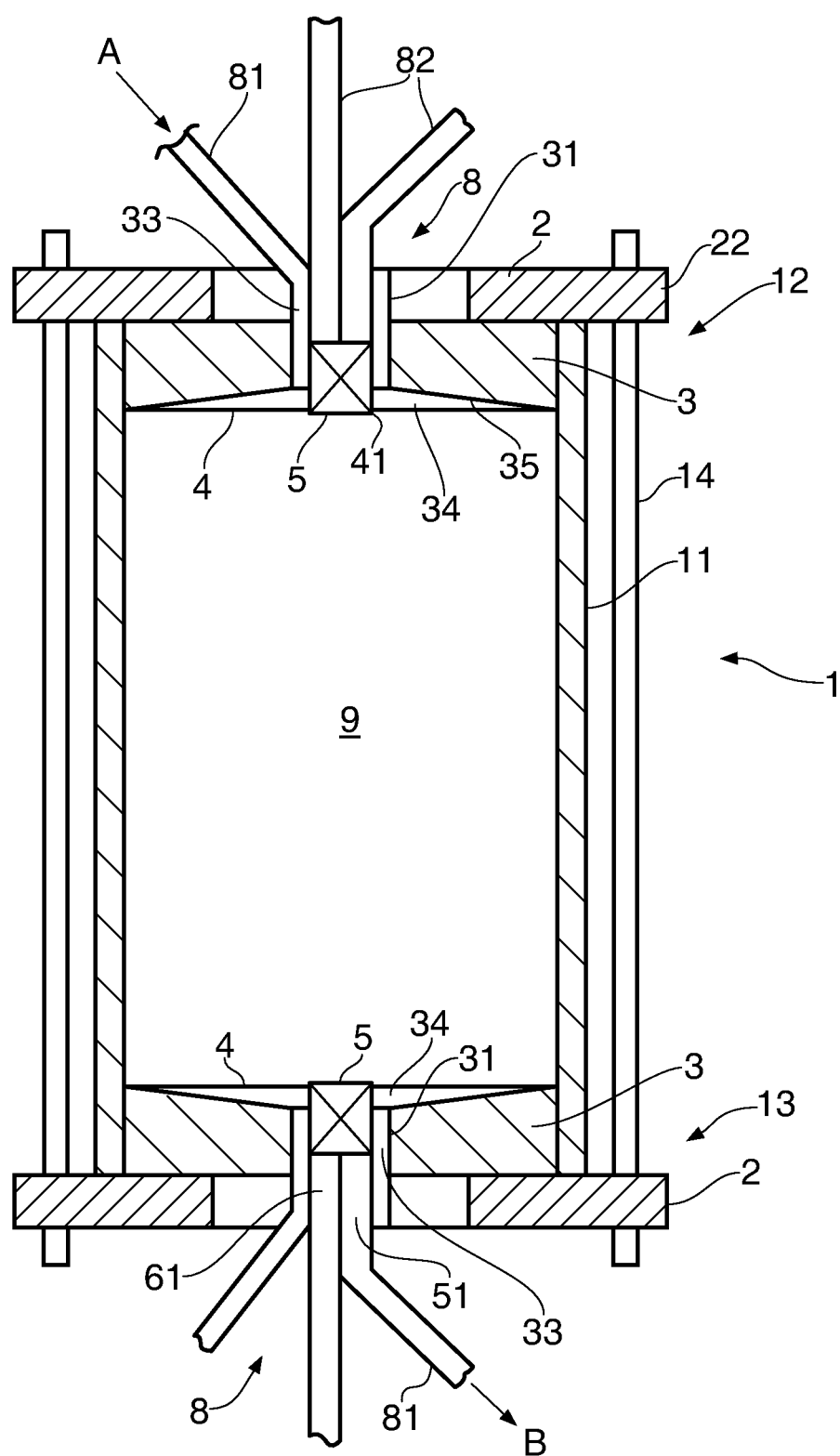
FIG. 1 is a schematic transverse sectional view of a chromatography column of the prior art showing the basic features thereof.

FIG. 1 shows schematically the general components of a chromatography column 1 as known from the prior art (for example, see U.S. Pat. No. 6,524,484). The column has a cylindrical fluid-impermeable side wall 11, e.g. of stainless steel or a high-strength/reinforced polymeric material which may be translucent. The open top and bottom ends of the side wall 11 are closed by top and bottom end assemblies or units 12, 13. Each end unit has a fluid-impermeable end plate 3 fitting sealingly to plug the opening of the cylindrical wall 11, and preferably made of stainless steel or high-strength engineering plastics material, e.g. polypropylene. The end plates are backed up by retaining metal plates 2 bearing against their outer surfaces and projecting radially beyond the side wall as retaining flanges 22 through which adjustable tension rods 14 are secured. These link the top and end assemblies 12, 13 and help the construction to withstand high fluid pressures.

Each end plate 3 has a central through-opening 31 for communication between the exterior of the column and the packing bed space 9 defined by the side wall 11 and end assemblies 12, 13. Access through the opening 31 is subdivided into separate conduits, connected externally through a connection manifold 8.

A filter layer 4, typically of filtered or woven plastics or steel, extends across the area of the bed space 9 at the inner surface of the end plate 3. The inner surface 35 of the end plate 3 is recessed behind the filter layer 4, e.g. conically as illustrated, and preferably with the use of support ribs (not indicated) supporting the filter layer 4 from behind, to define between them a distribution channel 34. One of the communication conduits, a mobile phase conduit 33, opens inwardly into this distribution channel 34, as well as outwardly to a mobile phase connector 81 of the manifold 8.

From the manifold 8, an access valve device 5 projects inwardly through the end plate opening 31 and sealingly through a central orifice 41 of the filter layer 4. The access valve 5, governs the communication of one or more conduits from the manifold 8 directly to the bed space 9, i.e. bypassing the filter layer 4. Indicated here are first and second valved conduits 51, 61 governed by the valve 5, and connected externally through connectors 82 of the manifold 8.

A packed bed of particulate stationary phase material fills the bed space 9 between the top and bottom filter layers 4. The packed bed may be formed by the "flow packing" method described above while the stationary phase is introduced into the bed space in the form of a slurry via access valve 5, preferably at the upper end piece of the of the column. The excess liquid passes through the bed, filter layer 4, distribution channel 34, conduit 33 and is removed through connector 81 (arrow B). As the stationary phase is retained by filter layer 4, the bed is growing throughout the process. Consolidation and subsequent compression take place under the influence of the seepage force (i.e. the reaction of the bed to the pressure gradient required to maintain the flow rate of the stream of liquid percolating through the bed). The growing bed is compressed substantially by introducing the slurry at a very high flow rate. By optimizing the packing flow rate, the desired compression factor can be achieved for the packed bed. Once the bed is compressed by the flow and the desired amount of stationary phase has been added to the column, the slurry flow is stopped and the access valve 5 is closed. This method does not require any adjustment of the upper end plate 3 such that the end plate is at a fixed bed height (target bed height) throughout the process.

An alternative method for compressing the bed of stationary phase is to apply mechanical axial compression by an axial movement of the adapter or end plate 3. This is achieved by means of a motor drive or hydraulic system attached to or built into the column (not shown in FIG. 1).

After column packing the valve devices 5 being closed, a mobile phase is fed in through mobile phase connector 81 (arrow "A"), passes through conduit 33 into the distribution channel 34 and through the filter layer 4 to elute down through the packed bed, effecting separation of its components or analytes. Liquid eluate passes thought the filter layer 4 of the bottom end assembly 13 and out through the mobile phase connector 81 thereof (arrow "B") for collection as appropriate. While this is an example of "downflow" chromatography, in that chromatographic separation is effected by the downward movement of the mobile phase through the column, the skilled person will understand that separation may alternatively be achieved by "upflow" chromatography, simply by pumping mobile phase upwards through the column and thus reversing the direction of flow. In this mode, mobile phase would enter the column at connector 81 (arrow "B"), move upwards through the stationary phase or particulate medium, and be collected from connector 81 (arrow "A") at the top of the column.

FIG. 1 and the above explanation are to illustrate general relationships of components and a typical mode of operation. The skilled person will understand, and it will also appear from the following description, that other specific constructions and modes of operation may be appropriate for different kinds of process.

Figure 2:
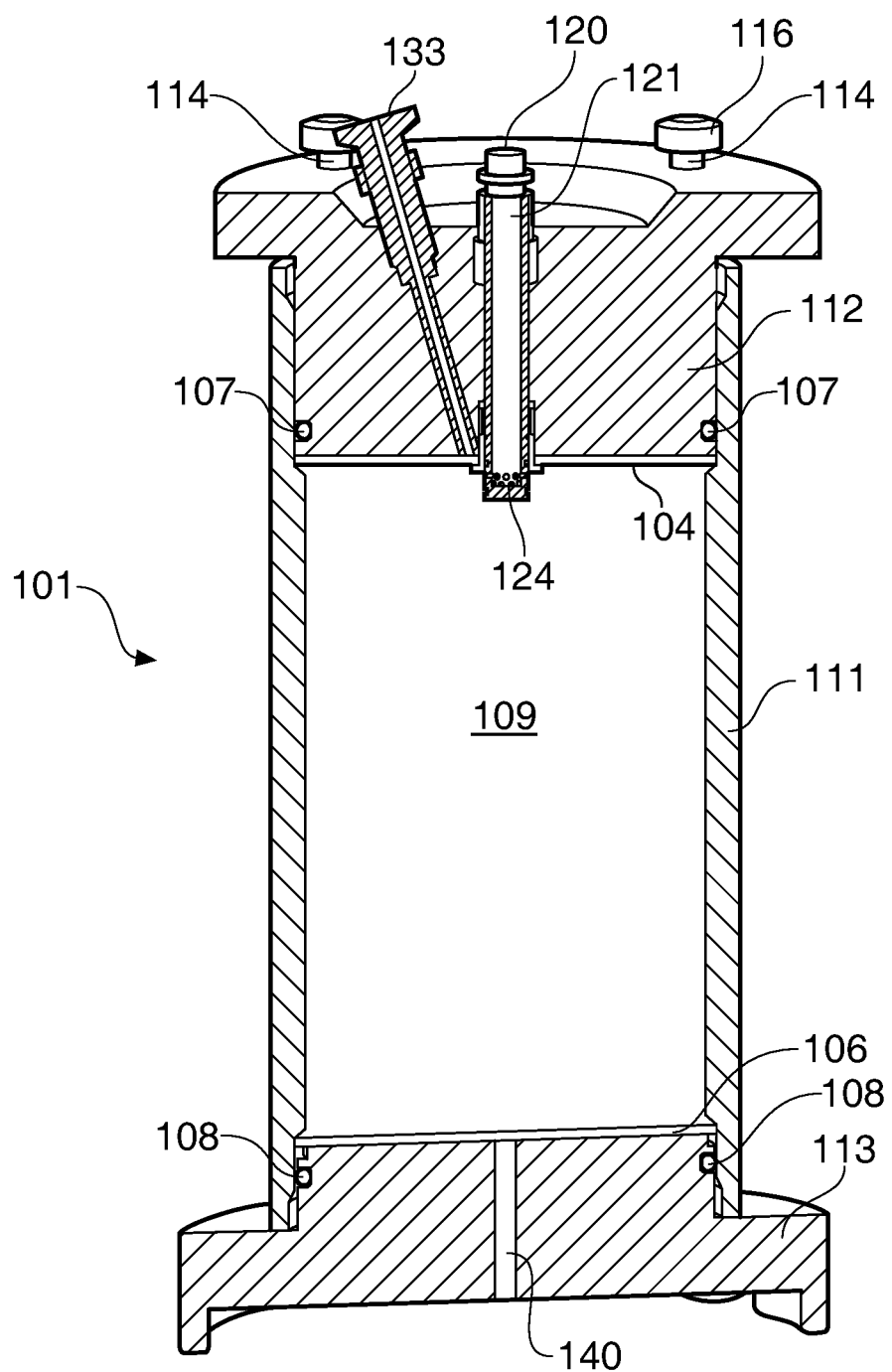
FIG. 2 is a three dimensional schematic showing a transverse sectional view of a chromatography column which can be packed using a method according to the invention.

FIG. 2 shows a transverse sectional view of a column in accordance with the invention. The column 101 comprises a tubular housing 111, a first end unit 112 (partially shown) and a second end unit 113, secured together to form a fluid tight seal by means of o-rings 107/108 and tension rods 114 having heads 116. First filter 104 and second filter 106 are adjacent to the first end unit 112 and second end unit 113, respectively. These filters 104, 106, together with side wall 111, define a bed space 109 for containing a bed of particulate medium.

The housing 111 and end units 112, 113 are typically composed of stainless steel or a high-strength plastic material such as polypropylene. In a preferred embodiment, where the column is to be used for the separation of biologically active substances, the material is biologically inert such that it does not elicit an immune response in humans in accordance with United States Pharmacopia (USP)<88> class VI. Tension rods 114, with heads 116, secure the end units 112, 113 to the housing 111 to form a fluid-tight bed space 109 which is capable of withstanding high operating pressures.

Filters 104, 106 are each positioned on the interior face of the end units 112, 113 and act to define the bed space (together with side wall 111) and to prevent leakage of particulate medium from the bed space 109. The end units 112 and 113 (and hence the first 104 and second 106 filters which are adjacent thereto) are axially movable in relation to each other. In FIG. 2, end unit 112 is axially movable within the housing 111 relative to the second end unit 113 but it will be understood that other embodiments are possible where one or both of the end units (and hence filters 104, 106) are axially movable relative to the other.

The bed space 109 is packed with a bed of particulate medium by first adjusting the height of the first end unit 112 such that the distance between the first 104 and second 106 filters is greater than the target bed height. In this state, the tie rods 114 and heads 116 are not attached to the column. The distance between the end units is secured by means of an external drive or compression frame (not shown). A slurry or suspension of particulate medium is then introduced into the column via valve means 120, the valve means comprising a central bore 121 and nozzle 124. At the same time as the suspension is being added to the bed space 109, excess liquid may also be removed from the bed space 109 via port 140 to produce a settled bed of particulate medium. After introduction of the desired amount of stationary phase, valve means 120 and nozzle 124 are closed. The settled bed is then compressed by the axial movement of the end unit 112 and filter 104 to achieve the target bed height, effected by an external drive or compression frame (not shown). The external drive, which is not an integral part or the column construction, may be controlled manually or by software means in order to achieve the desired target bed height. The end units are then secured against each other by help of the tie rods (114) and heads (116), respectively, and the column is then released from the external drive or compression frame.

In FIG. 2 the nozzle 124 is shown in its filling position being exposed to the bed space 109 but it will be understood that it can be retracted to a closed position within the top end plate 112 after filling of the column. The nozzle 124 and valve means 120 are locked in either open or closed position by a locking device (not shown). A wide range of nozzles can be used which facilitate the distribution and even packing of slurry within the bed space. One alternative for achieving an open/closed functionality at the packing valve and nozzle respectively is to have a nozzle that is fixed in the bed space (and thus not retractable) and located adjacent to a moveable element or sleeve on the inside or outside of the nozzle that opens and/or closes the nozzle depending upon its position.

Mobile phase or liquid containing one or more analytes or substances for separation on the column is added via first port 133. The liquid then passes through the first filter 104 into the bed space 109 that has been packed with particulate medium as described above. Chromatographic separation of analyte(s) which has been introduced onto the particulate medium in this manner is effected by introduction of, and elution by, mobile phase. The mobile phase will finally exit the column through second filter 106 and via second port 140. The resulting fractions of mobile phase, which contain different analytes, can then be collected.

It will be understood by the skilled person that the column may be operated in either a "downflow" mode, as described above, or in an "upflow" mode where the direction of flow of the mobile phase is reversed such that it moves up the column. In upflow mode, mobile phase will enter the column via second port 140, move upwards through the bed of particulate medium in bed space 109, to exit the column for collection at first port 133.

Figure 3:
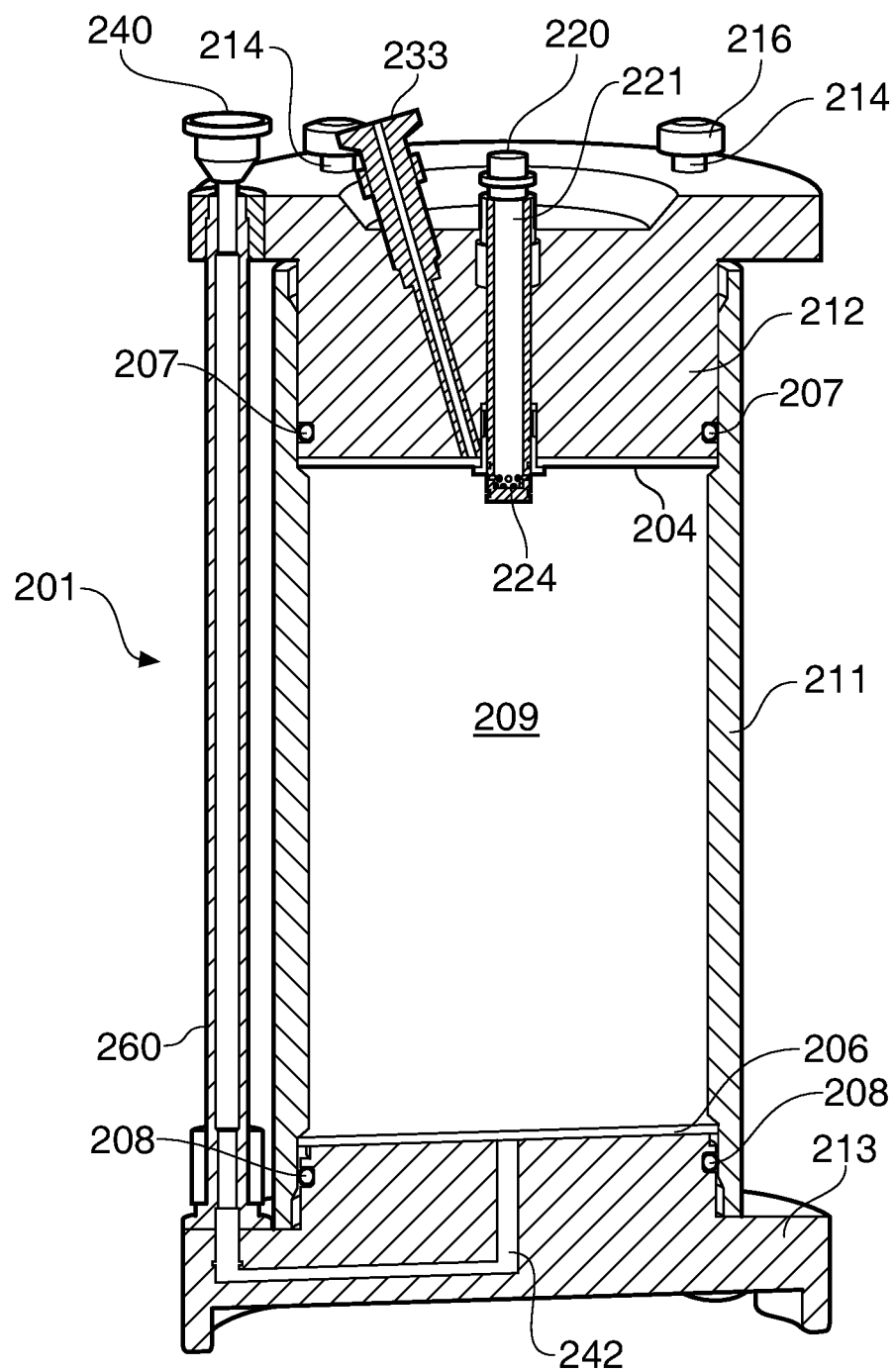
FIG. 3 shows a three dimensional schematic showing a transverse sectional view of a different embodiment of a chromatographic column which can be packed using a method in accordance with the invention.

FIG. 3 is a transverse sectional view of a column in accordance with the invention. The column is similar to the column of FIG. 2, with many of the features being identical to those described in that figure. Thus the column has a valve means 220 for the addition of a suspension of particulate medium into a bed space 209 and a first port 233 for the addition or collection of mobile phase. However, the column differs from that embodiment previously described in that it has a second port 240 comprising a passageway 242 which extends through second end unit 213 to, and is in fluid communication with (via hollow member 260), bed space 209 from which liquid can be added or collected. As is evident from the figure, the second port 240 is at essentially the same level or elevation as the first port 233, thus facilitating the addition and collection of mobile phase to/from the column. This arrangement has further advantages in that it assists in the installation of the column, decreases the risk of siphoning and reduces the likelihood of introduction of air into the column.

The arrangement of the component parts are otherwise as described in FIG. 2. The column 201 comprises a tubular housing 211, a first end unit 212 (partially shown) and a second end unit 213, secured together to form a fluid tight seal by means of o-rings 207/208 and tension rods 214 with heads 216. First filter 204 and second filter 206 are adjacent to the first end unit 212 and second end unit 213, respectively. These filters 204, 206, together with side wall 211, define a bed space 209 for containing a bed of particulate medium. The first end unit 212 and the second end unit 213 are axially movable with respect to each other by means of an external drive (not shown) such as an actuator, press or frame which may be operated manually or automatically under the control of software. The filters 204, 206 are adjacent to the first end unit 212 and second end unit 213 and are axially movable with the end units relative to each other. In the embodiment shown, only end unit 212 and first filter 204 are axially movable relative to the second end unit 213 and filter 206 but it will be understood that other embodiments are possible wherein either or both of the end units and filters are axially movable relative to the other.

The column is packed with a bed of particulate medium to a target bed height as described in FIG. 2. The height of the first end unit 212 is adjusted such that the distance between the first 204 and second 206 filters is greater than the target bed height by means of an external drive (not shown). A slurry or suspension of particulate medium is then introduced into the column via valve means 220, the valve means comprising a central bore 221 and nozzle 224. Excess liquid may be removed from the bed space 209 via passageway 242 and port 240 to produce a settled bed of particulate medium. The settled bed is then compressed by the axial movement of the end unit 212 and filter 204, effected by the external drive (not shown), to achieve the target bed height. The external drive may be controlled manually or by software means in order to achieve the desired target bed height. The end units are then secured against each other by help of the tie rods (214) and heads (216), respectively.

Mobile phase or liquid containing one or more analytes or substances for separation on the column is added via first port 233. The liquid then passes through the filter 204 into the bed space 209 that is packed with particulate medium as describe above. Chromatographic separation of analyte(s) which has been introduced onto the particulate medium in this manner is effected by introduction of, and elution by, mobile phase. The mobile phase will finally exit the column through second filter 206 and via passageway 242 to second port 240. The resulting fractions of mobile phase, which contain different analytes, can then be collected.

It will be understood by the skilled person that the column may be operated in either a "downflow" mode, as described above, or in an "upflow" mode where the direction of flow of the mobile phase is reversed such that it moves up the column. In upflow mode, mobile phase will enter the column via second port 240, move along passageway 242 and upwards through the bed of particulate medium in bed space 209, to exit the column for collection at first port 233.

In the embodiment shown, hollow member 260 is an integral part of the column. However, it will be understood that by means of connectors and appropriate tubing made from a suitable material (e.g. polypropylene, polyurethane, etc.) that the hollow member 260 need not be integral to the column.

The application and collection of mobile phase at the same elevation on a single end unit simplifies use, in terms of operator access and handling, reduces the risk of air accessing the system and decreases the space necessary to set up the column.

Figure 4:
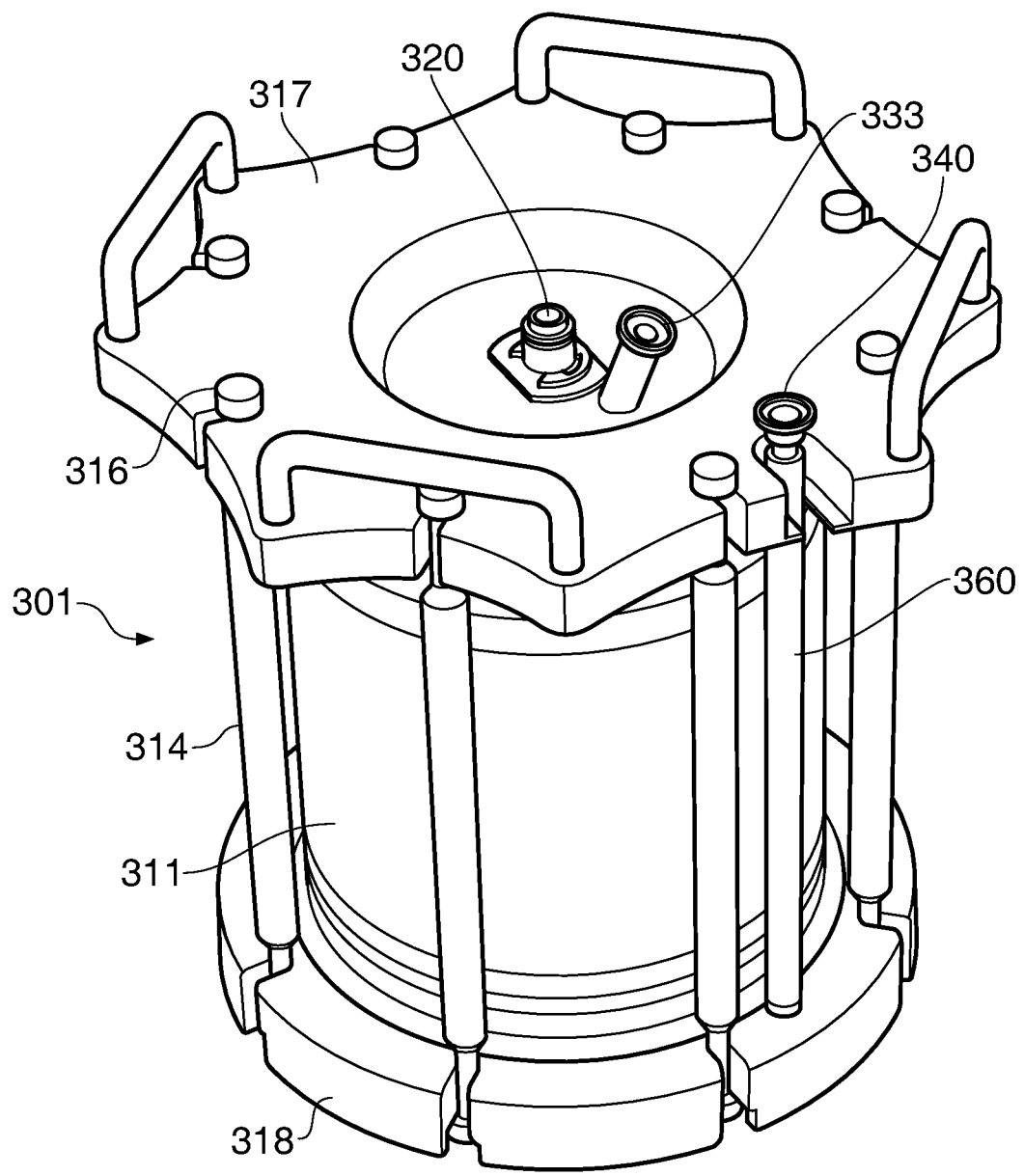
FIG. 4 is a three-dimensional schematic of a chromatography column packed using a method in accordance with the invention.

FIG. 4 presents a three dimensional schematic representation of column of FIG. 3 of larger column diameter, from which the external features of the column are evident. The column comprises a first end unit 317, which is movable during the compression step, second end unit 318 and housing 311 which are secured together to form a fluid-tight seal by tension rods 314 and heads 316. Particulate medium in the form of a slurry can be introduced into the bed space (not shown) via valve means 320. First port 333 serves as a conduit for mobile phase or liquid containing analyte(s) to be separated on the particulate medium. Hollow member 360, which is in fluid communication with the bed space via an outlet at the base of the column (not shown), ends in second port 340 from which appropriate fractions of mobile phase eluted from the column may be collected. As can be seen, second port 340 is at essentially the same level or elevation as the first port 333 through which mobile phase can be introduced (or collected). This arrangement facilitates user operation and sample handling. In the embodiment shown in FIG. 4, the capacity of the column is approximately 10 litres; it will be understood that a wide range of column capacities is possible, typically ranging from 0.1 to 2000 litres. Preferred capacities when using the column as a disposable column are in the range of 0.5 to 50 litres.

Figure 5:
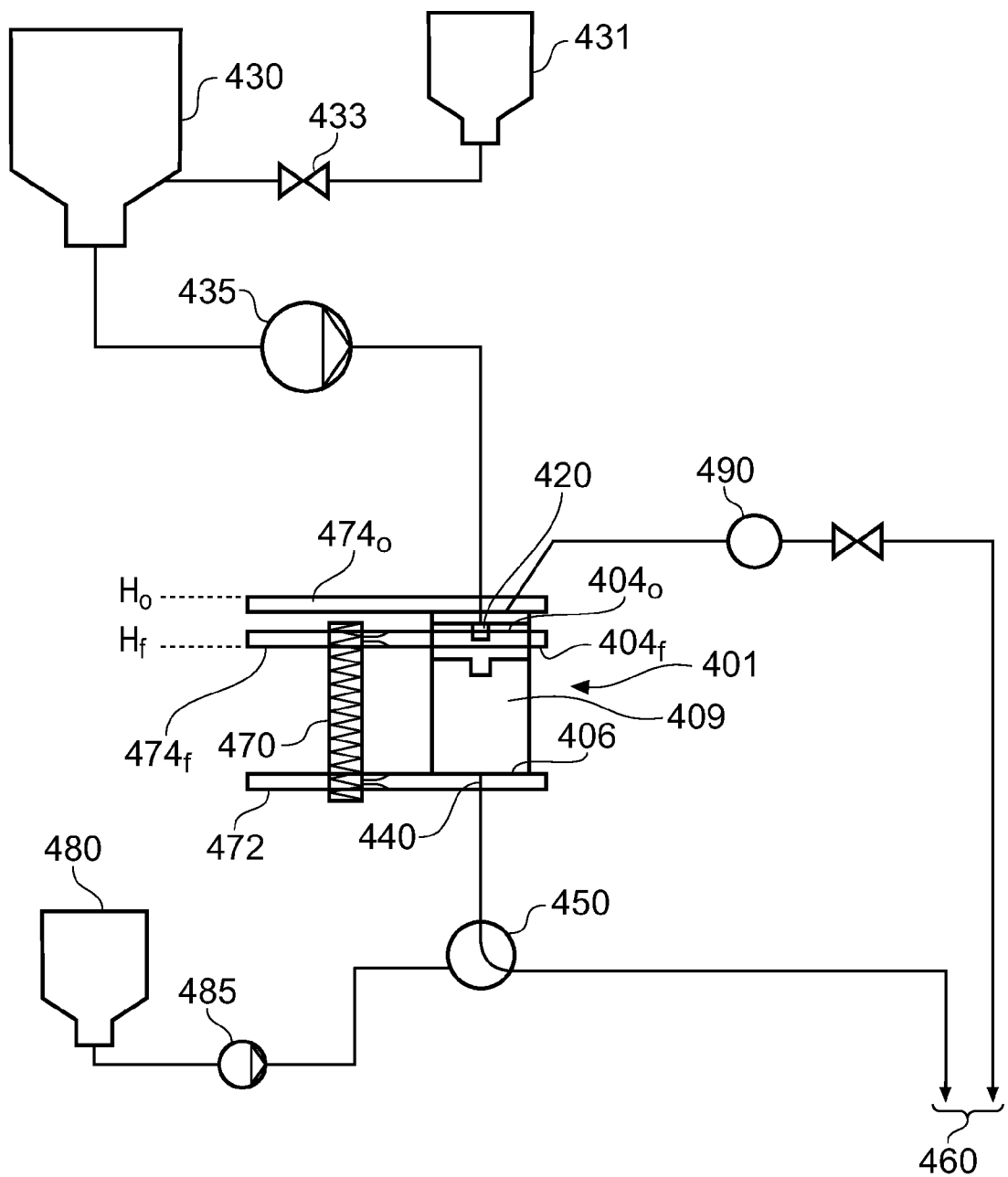
FIG. 5 is a schematic illustration of a system for packing an axial flow chromatography column using a method in accordance with the invention.

FIG. 5 is a schematic illustration of a system for packing an axial flow chromatography column using a method in accordance with the invention. The system comprises a column 401 as described in FIG. 2 above. The column is connected to an external drive means 470 (such as a compression frame) which, by means of platforms 472 and 474 can adjust the height of an axially movable first end unit (not shown) and first filter (404) within the bed space 409 of the column relative to a second end unit (not shown) and second filter 406.

The system is initially primed with liquid from container 480 via pump 485 which is in fluid communication with outlet valve 450 to facilitate the removal of air from the column or from at least the bottom distribution system and filter layer. Excess liquid or air may be removed from the column via the upper inlet/outlet port of the column 401 to exit as waste 460. Pressure sensor 490 monitors pressure within the column during the priming phase and/or subsequent packing phase.

The first end unit and filter 404 are initially adjusted to position $H_o$ (shown as $474_O$ in the figure) such that the distance between the first and second filters 404, 406 is greater than that of the target bed height within the bed space 409. Particulate medium, in the form of a slurry or suspension within container 430, is then introduced into the column bed space 409 under pressure by pump 435 through inlet valve 420. Any residual slurry remaining within container 430 can be washed into the bed space 409 by rinsing the container 430 with a packing liquid from reservoir 431 via valve 433. At the same time as slurry is being introduced into the bed space 409, excess liquid may be removed via outlet 440 in order to produce a settled bed of medium within the bed space. The excess liquid passes through outlet valve 450 and thence is voided as waste 460. During the consolidation step the pressure in the column bed space 409 is monitored by sensor 490 and can be regulated by adjusting the flow rate of pump 435 in order to achieve different degrees of pre-compression of the packed bed.

Finally, compression of the bed to its target bed height is achieved by lowering the platform 474 to position $H_F$ (shown as $474_F$ in the figure) which causes axial movement of the first filter 404 relative to the second filter 406. Depending on the type of chromatography medium, the packing process may be controlled to different degrees of pre-compression by flow packing and final compression by axial compression. After lowering the upper end unit to the final position $H_F$, the column end units are secured by means of the tie rods and the column can be released from the compression frame.

FIG. 5 and the above explanation are to illustrate the method of packing the columns. The skilled person will understand that other arrangements of pumps, vessels and sensors are possible. The use of disposable liquid handling equipment, like bags and tubing, is preferred when packing disposable columns that shall fulfill requirements on a controlled level of microbiological burden or columns that shall be produced under aseptic conditions.

In one embodiment a sterile column is produced by packing columns under aseptic conditions by using pre-sterilized components such as column housing, medium, process fluids, fluid lines, vessels, containers, bags, sensors. Methods of pre-sterilisation include autoclaving, steaming (in place), gamma irradiation, E-Beam irradiation, chemical sterilization (i.e. ethylene oxide) or other methods. The production of columns under aseptic conditions using pre-sterilized components is for example preferable if the application of different sterilization methods for the different components of the packed column are preferable or required. For example, the effective pre-sterilisation of chromatography medium may be done by autoclaving, while autoclaving may be prohibitive as a method of sterilization for a disposable column housing made of plastic materials for reason of cost efficiency and disposability, the latter for example being the full compatibility with incineration methods for post use destruction and disposal. In another example, the effective pre-sterilisation of chromatography medium may require the chromatography medium being sterilized in a certain volume or container shape to uniformly and gently apply the sterilization effect. Thus, the container or bag used for the pre-sterilisation process may be optimized for the sterilization and different from the shape and volume of the final column otherwise deployed for a sterilization after production of a packed column.

When producing a sterile column under aseptic conditions, said components in contact with medium and processing fluid used in the process are pre-sterilized, too. For connecting and disconnecting components welding methods may be used. Preferably, sterile connectors and disconnectors are used for connecting and disconnecting components, such as for example ReadyMate connectors (GE Healthcare).

In one embodiment of the invention an aseptic packed column is achieved by packing a pre-sterilized axial flow chromatography column with a bed of pre-sterilized particulate medium of a target bed height. Said column comprises a housing comprising an elongated tubular side wall and opposed, axially spaced first and second end units separated by said side wall. At least one said unit is axially movable by drive means relative to the other said unit. Said drive units could be non-integral to and external to the column or alternatively said drive means could be integral to the column. Said column further comprises a first filter adjacent to said first unit and a second filter adjacent to said second unit which together with the side wall define an enclosed bed space for containing a bed of particulate medium and wherein relative movement of the first and/or second filter alters the bed height. Said first end unit comprises a first valve means for filling of the bed space with said particulate medium and a first port for adding a liquid to or removing a liquid from the bed space. The second end unit comprises a second port for adding a liquid to or removing a liquid from the bed space.

The packing method comprises:
i. adjusting the axial spacing between the first and second filters to a distance greater than that of the target bed height;
ii. introducing a suspension of the pre-sterilized particulate medium into the bed space via the first valve means to provide a bed of particulate medium therein;
iii. compressing said bed of particulate medium to produce the target bed height by axial movement of the first and/or second end filters.

This described packing method where pre-sterilized particulate medium is provided into a pre-sterilized column will provide an aseptic packed column. Suitable aseptic, disposable components are used, like bags, tubing and connectors.

Either external drive means together with tie rods can be used as described above. However in this embodiment a drive means that is integrated into the column could alternatively be used. Such drive means could be for example in the form of an hydraulic chamber in the column adjacent to a movable adapter. Here, the adapter may be fixed mechanically (locking ring, tie bars etc.) after the hydraulic action and adjuster adjustment so that the chamber may be drained from liquid. Another alternative could be to use threaded tie bars that allow a mechanical adjustment of the adapter height by adjustment of the nuts on the tie bar. Here, the tie bar could be built from segments such that an extending segment used for the adapter movement is removed after the adapter adjustment. Another alternative would be to use spring loaded adapter movement, whereby the final adapter position may be pre-defined by a mechanical stop hereby limiting the stroke due to the spring action. The spring action may be mechanically released to initiate the adapter movement. By throttling the fluid flow of the excess fluid removed from the column space during the adapter movement, the speed of movement can be controlled. Further the final position of the adapter can be controlled temporarily by blocking the flow of said excess liquid such that a mechanical locking mechanism can be brought in place. Other alternatives of driving means could be hydraulic cylinders or electrical drive motor.

The principle of pre-sterilizing the chromatography column before an already pre-sterilized chromatography media is introduced to the column via aseptic equipment can be adopted also for other types of chromatography columns than has been described above. For example this would be suitable also for chromatography columns without driving means where the packing is provided by introducing chromatography media slurry through the nozzle into the column having a fixed volume. If an adaptor is provided the adapter has been provided at the wanted bed height beforehand. The slurry is provided into the column until the bed is packed.

The present invention is also related to a method for providing an aseptic chromatography column where said method comprises the steps of:
pre-sterilize an empty chromatography column;
pre-sterilize a chromatography medium;
introducing the pre-sterilized chromatography medium into the pre-sterilized chromatography column using aseptic equipment, thereby providing an aseptic chromatography column comprising chromatography medium.

With this method it is possible to use different types or different intensities of sterilization for the sterilization of the column and the media.

The method for pre-sterilization of the chromatography column and the method for pre-sterilisation of the chromatography medium can be selected from at least one of the different methods of sterilization such as heat sterilization by autoclaving or steaming (in place), chemical sterilization (i.e. ethylene oxide), gamma irradiation or eBeam irradiation.

In one embodiment of the invention the method for sterilization used for the pre-sterilization of the chromatography column is different from the method for sterilization used for the pre-sterilization of the chromatography medium. This can be advantageous when one method for sterilization is not suitable for sterilizing both the column and the media. For example gamma radiation may be a suitable method for sterilizing the chromatography column but not for sterilizing the media or autoclaving may be suitable method for sterilization for the media but not for the column, especially when plastic materials are used as method of construction.

In one embodiment of the invention the method for pre-sterilization of the chromatography column and the method for pre-sterilisation of the chromatography medium are the same whereby the intensity of protocol for performing the pre-sterilisation using said method are different.

The invention is also related to an aseptic chromatography column comprising chromatography medium wherein the chromatography column has been pre-sterilized separately and the chromatography medium has been pre-sterilized separately before introduction into the chromatography column.

In one embodiment of the invention the pre-sterilization of chromatography medium is performed on dry chromatography medium. The pre-sterilized dry chromatography medium can be re-suspended before packing the pre-sterilized column. In one embodiment, the dry chromatography medium is introduced in its dry state into the column and wetted inside the column space after introduction into the column.

Figure 6:
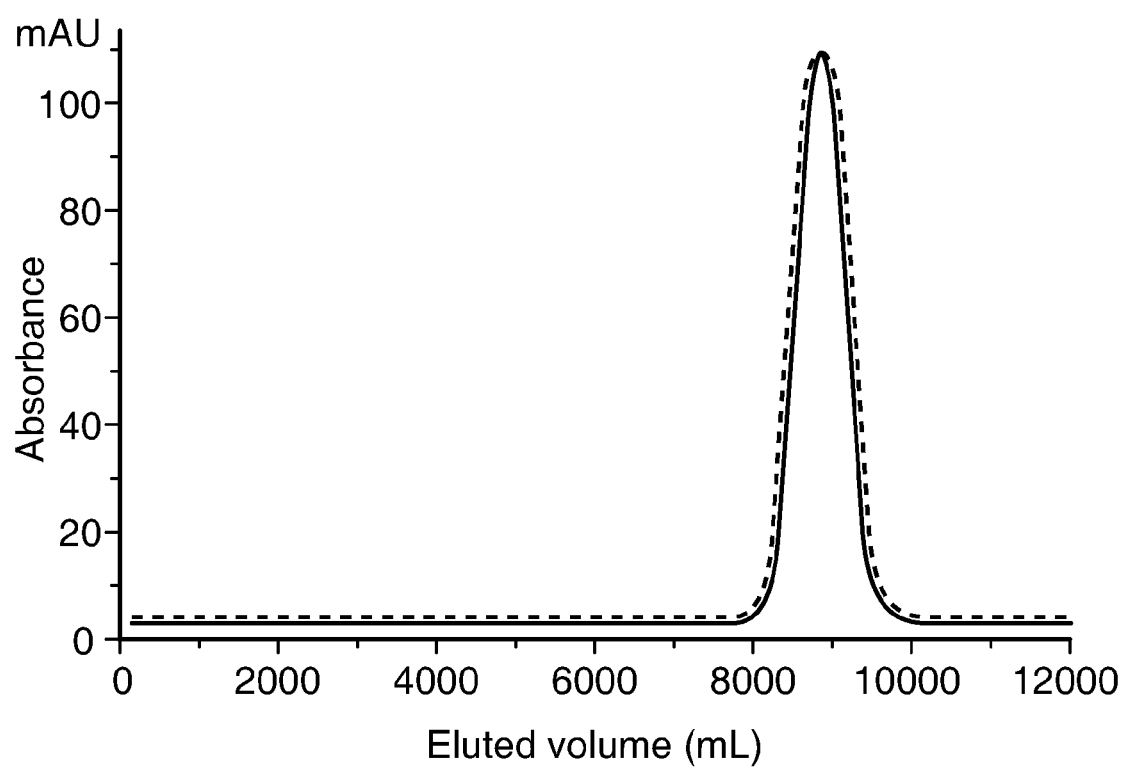
FIG. 6 is a chromatogram showing the chromatographic separation of acetone on a chromatography column packed in accordance with the invention, both in upflow (dotted line) and downflow (solid line) mode.

FIG. 6 shows the chromatographic separation efficiency by example of a tracer pulse experiment achieved on a 10 litre column in accordance with the invention, operated in both downflow (solid line) and upflow (dotted line) mode. The column was packed with a bed of Capto™ Q anion exchange resin (GE Healthcare, Uppsala, Sweden) of 85 μm agarose particle diameter using the method according to the invention. The column had a volume of 10.8 L, a diameter of 263 mm and a bed height of 200 mm. Acetone (1% of packed bed volume) was used as a tracer substance and eluted from the column using water as mobile phase and the absorbance monitored at 280 nm. As can be seen from Table 1 below, excellent column efficiency was observed with the 85 μm agarose medium used, either in downflow (solid line) or upflow (dotted line) mode.

TABLE 1

|  | Observed | Acceptance |
|---|---|---|
| Plates/meter (N/m) | 4430 | >3700 (for 85 μm) |
| Reduced plate height (h) | 2.5 | <3.0 |
| Peak asymmetry (Af) | 1.14 | 0.8-1.8 |

The data from Table 1 were derived from the chromatogram of FIG. 6 as described below.

Figure 7:
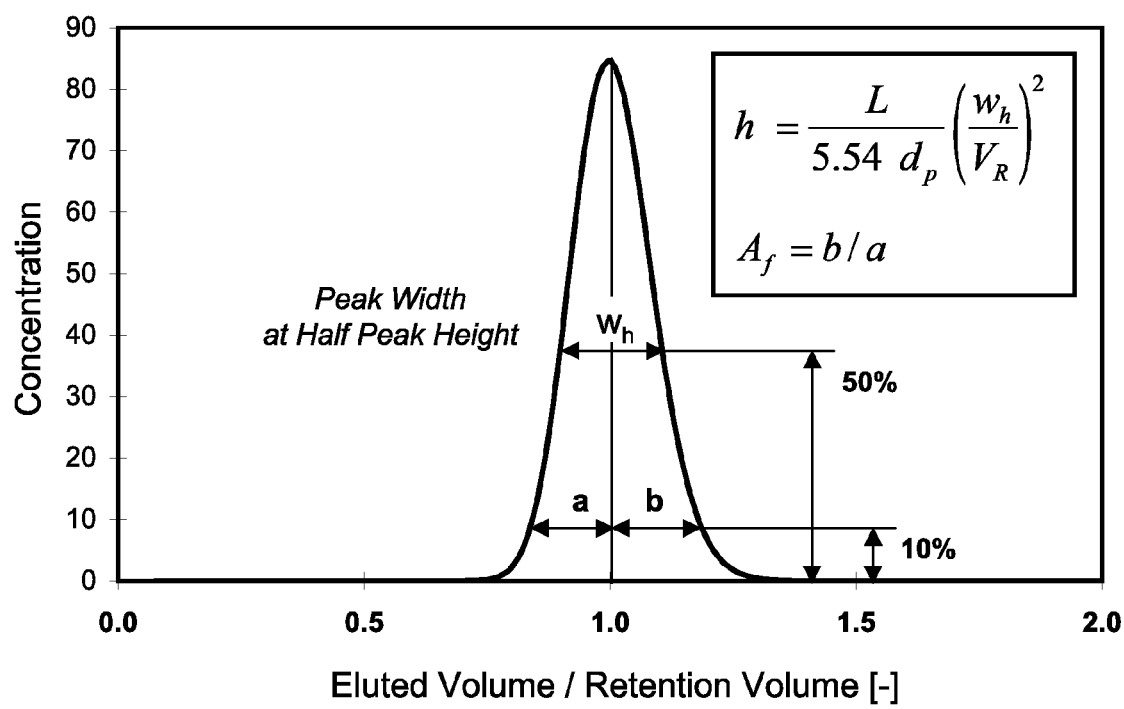
FIG. 7 describes a method for calculating the reduced plate height and asymmetry factor from an eluted peak.

As a measure for column efficiency, the reduced plate height is determined with help of the peak width $w_h$ at half the height of the eluted peak, as shown in FIG. 7. This procedure is an approximation valid for a peak with Gaussian shape. In practice, eluted peaks often deviate from this ideal gaussian shape and peak skewness is described qualitatively by a so-called asymmetry factor $A_f$, where 'leading' in the RTD is indicated by $A_f<1$ and 'tailing' by $A_f>1$. Commonly applied acceptance criteria for the asymmetry factor are $0.8<A_f<1.5-1.8$, depending on the type of application.

$$h = \frac{HETP}{d_P} = \frac{L}{d_p}\frac{1}{5.54}\left(\frac{w_h}{V_R}\right)^2$$

$A_f = b/a$ (see FIG. 7)
$A_f$ asymmetry factor
$d_p$ particle diameter
h reduced plate height
HETP height equivalent of a theoretical plate
L bed height, packed bed
$u_s$ superficial velocity in packed bed
$V_R$ retention volume
$w_h$ peak width at 50% of max. peak height

The invention claimed is:

1. A method for packing an axial flow chromatography column with a bed of particulate medium of a target bed height, the method comprising:
   i. providing a chromatography column comprising:
      a housing comprising an elongated tubular side wall;
      opposed, axially spaced first and second end units forming external surfaces of the chromatography column and separated by said side wall, wherein at least one of said first and second end units is axially movable in the column by an external drive;
      a first filter adjacent to said first end unit and a second filter adjacent to said second end unit which together with the side wall define an enclosed bed space for containing a bed of particulate medium and wherein relative movement of the first and/or second filter alters the bed height, the first filter extends across an area of the bed space along an inner surface of the first end unit;
      said first end unit extending above the side wall and comprising a first valve extending through the first filter, for filling the bed space with said particulate medium; and a first port for adding a liquid to or removing a liquid from the bed space;
      said second end unit comprising a second port for adding liquid to or removing liquid from the bed space;
   ii. controllably adjusting by the external drive having a mobile platform attached to the first end unit, a position of one of the first end unit and the first filter to a specific position such that the axial spacing between the first filter and the second filter is adjusted to a distance greater than that of the target bed height wherein the first end unit is spaced a predetermined distance above the side wall;
   iii. introducing a suspension of the particulate medium into the bed space via the first valve to provide a compressed bed of particulate medium therein; and
   iv. compressing said bed of particulate medium to produce the target bed height by performing axial movement of the first end unit and the first filter to decrease the distance to the target bed height until the first end unit rests on the side wall;
      wherein said axial flow chromatography column and said suspension of particulate medium are pre-sterilized.

2. The method of claim 1, wherein step iii) is achieved by said external drive which is non-integral to and is external to the column.

3. The method of claim 2, wherein said external drive is selected from one of a group of drives consisting of an actuator, a press and a frame.

4. The method of claim 1, wherein the particulate medium is a chromatography medium selected from the group consisting of ion exchange medium, reverse phase medium, size exclusion medium and affinity medium.

5. The method of claim 1, wherein the first valve is a one way valve.

6. The method of claim 1, wherein the column is a disposable column.

7. The method of claim 1, wherein step iii) additionally comprises the step of removing excess liquid from the bed space while introducing the suspension of the particulate medium into the bed space via the first valve to thereby produce a settled bed of particulate medium therein.

8. The method according to claim 1, further comprising the steps of:
securing the first end unit against the second end unit by means of tie rods; releasing the column from the drive.

* * * * *